March 28, 1972 T. HEGG Plant Pat. 3,082
POINSETTIA PLANT
Filed Jan. 21, 1970
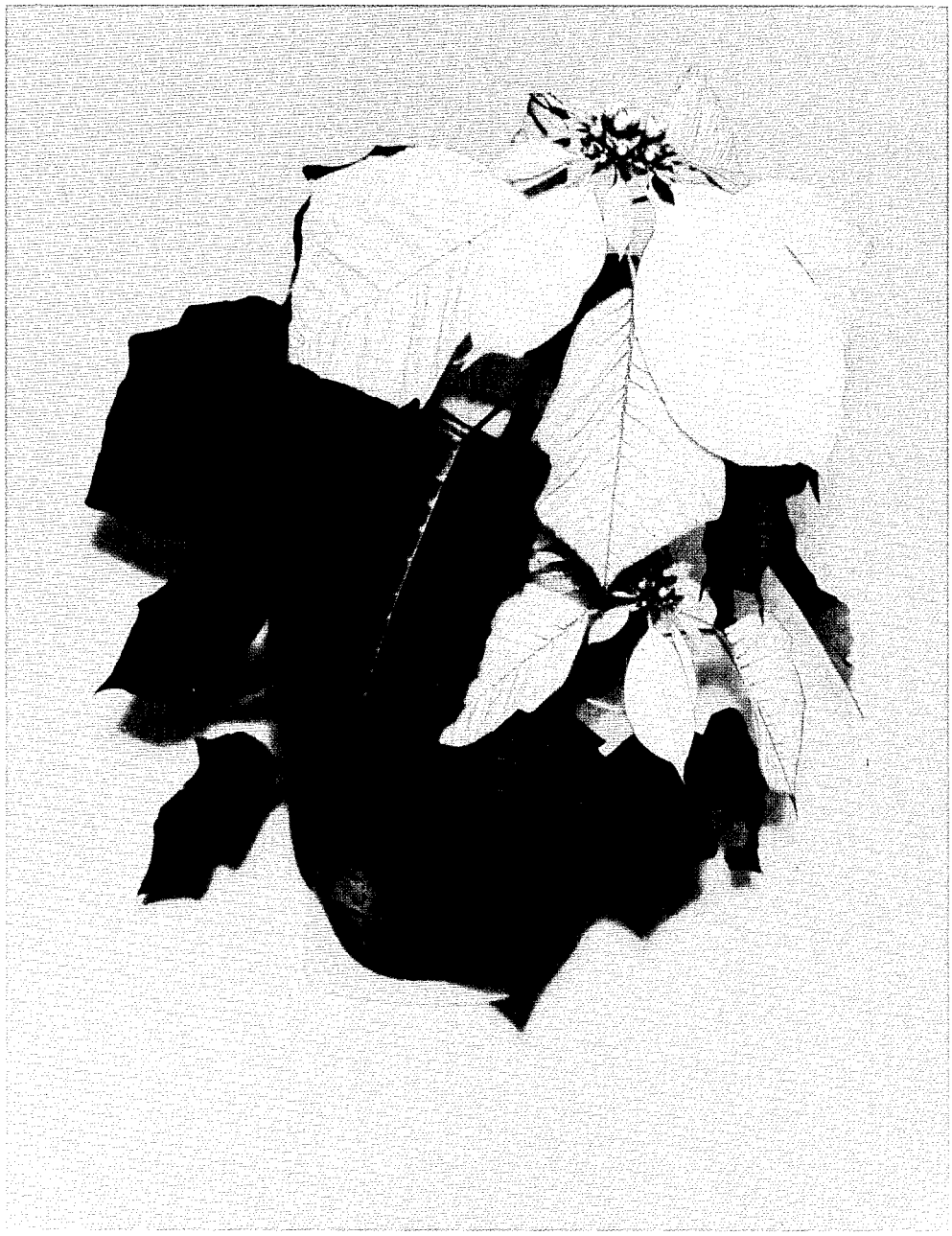
Inventor.
Thormod Hegg
By: Robb & Robb
attorneys.

United States Patent Office

Plant Pat. 3,082
Patented Mar. 28, 1972

3,082

POINSETTIA PLANT

Thormod Hegg, Lierbyen, Norway, assignor to Paul Ecke, Inc., Encinitas, Calif.

Filed Jan. 21, 1970, Ser. No. 4,787
Int. Cl. A01h *5/00*
U.S. Cl. Plt.—86 1 Claim

The present invention relates to a new and distinct variety of poinsettia plant, botanically known as *Euphorbia pulcherrima,* which was discovered by me as a cultivated sport of the poinsettia variety known as "Annette Hegg" (U.S. Plant Pat. No. 2,962), said discovery having been made by me in my greenhouses at Lier, Norway.

At the time of my discovery aforesaid, I was growing various poinsettia varieties, including many plants of the variety "Annette Hegg." During these growing operations which were being conducted under my personal supervision and care, my attention was attracted to one particular plant among those of "Annette Hegg" which bore bracts of white color instead of the normal red bracts of "Annette Hegg." Close inspection of this particular plant showed that it had sported, and I accordingly took steps to carefully preserve the sport and keep it under close observation. Shortly after my discovery, I asexually reproduced the sport by vegetative cuttings taken therefrom by me and grown in my greenhouse at Lier. Continued observations and tests of the original sport and its progeny derived therefrom as aforesaid, fully confirmed that the white bracts come true, along with all other characteristics which are otherwise substantially identical with those of the parent variety "Annette Hegg." This has been further confirmed by extensive tests and observations conducted on my behalf at Encinitas, Calif., U.S.A. I am convinced from all of these tests and observations that my white-bracted sport represents a new and distinct poinsettia variety, as evidenced by being substantially identical in all respects to the variety "Annette Hegg" except for the white bract color which definitely distinguishes it therefrom and from all other varieties of which I am aware, with the most outstanding characteristics of the new variety being summarized by the following combination of unique and commercially valuable features:

(1) A short growing and compact plant habit;
(2) A uniform and fast rooting habit;
(3) A self-branching habit which results in the production of multiple blooms without pinching off the terminal buds;
(4) Attractive green foliage;
(5) Distinctive and attractive white bracts which create a striking contrast with the green foilage; and
(6) Long-lasting plant qualities.

The accompanying drawing shows a typical specimen plant of my new poinsettia variety as illustrated in color as nearly true as it is reasonably possible to make the same in a color illustration of this character.

Although, except for the bract color, the details of the new sport substantially conform to the description embodied in U.S. Plant Pat. No. 2,962, to which reference may be readily had, the following brief description thereof is given for convenience, with color terminology being in accordance with Wilson's Horticultural Colour Chart, except where general color terms of ordinary dictionary significance are obvious:

Locality where grown and observed: Lier, Norway, and also Encinitas, Calif., U.S.A.
Form: Short growing; compact.
Habit of growth: Self-branching; produces multiple blooms without pinching off terminal buds.
Rooting habit: Very uniform; very fast.
Blooming habit: Very predictable; 9-week variety.
Blooming season: Blooms predictably in time for Christmas season and well beyond through at least the month of April; also good for flowering in spring, summer and autumn.
Foliage:
*Shape.*—Usually ovate—acuminate; seldom lobed. Color.—New foliage: Upper side—Pod Green, Plate 061. Lower side—Pod green, Plate 061/1. Old foliage: Upper side—Spinach Green, Plate 0960. Lower side—Spinach Green, Plate 0960/2.
Bracts: Ovate; relatively broad.
*Color.*—White.
Reproductive organs:
*Stamens.*—Quite numerous; from about ⅛ inch to ¼ inch long.
*Pollen.*—Color—Canary Yellow, Plate 2.
*Styles.*—Color—Blood Red, Plate 820.
*Ovaries.*—Color—Scheele's Green, Plate 860/1.
*Nectar cups.*—Color—Lemon Yellow.

I claim:

1. A new and distinct variety of poinsettia plant, substantially as herein shown and described, characterized particularly as to novelty by being substantially identical in all respects to the poinsettia variety known as "Annette Hegg" (U.S. Plant Pat. No. 2,962) except for its bract color, with the bracts having a distinctive and attractive white color as essentially distinguished from the red bracts of the variety "Annette Hegg."

No references cited.

ROBERT E. BAGWILL, Primary Examiner